United States Patent [19]

Hofmann et al.

[11] Patent Number: 5,021,056
[45] Date of Patent: Jun. 4, 1991

[54] UPPER TIBIAL OSTEOTOMY SYSTEM

[75] Inventors: Aaron A. Hofmann, Salt Lake City, Utah; Albert G. Burdulis, Jr., Austin, Tex.

[73] Assignee: Intermedics Orthopedics, Inc., Austin, Tex.

[21] Appl. No.: 407,244

[22] Filed: Sep. 14, 1989

[51] Int. Cl.⁵ .............................................. A61F 5/04
[52] U.S. Cl. .................................................... 606/86
[58] Field of Search ............... 606/86, 87, 88, 79, 606/82; 623/16, 66

[56] References Cited

U.S. PATENT DOCUMENTS

| | | | |
|---|---|---|---|
| 4,335,715 | 6/1982 | Kirkley | 128/92 EB |
| 4,501,268 | 2/1985 | Comparetto | 128/92 E |
| 4,509,511 | 4/1985 | Neufeld | 128/92 H |
| 4,565,191 | 1/1986 | Slocum | 128/92 H |
| 4,627,425 | 12/1986 | Reese | 128/92 VY |
| 4,632,102 | 12/1987 | Comparetto | 128/92 VY |
| 4,736,737 | 4/1988 | Fargie | 128/92 VY |
| 4,750,481 | 6/1988 | Reese | 128/92 VY |
| 4,757,810 | 7/1988 | Reese | 128/92 VY |

Primary Examiner—David J. Isabella
Attorney, Agent, or Firm—John R. Merkling

[57] ABSTRACT

A method and apparatus for performing an upper tibia osteotomy comprising cutting a wedge from the bone using a first guide assembly to cut a first slot partially through a bone and a second guide assembly to cut a second intersecting slot to define a wedge shaped bone segment. An external compressor device draws the osteotomy closed by plastic deformation of the unsevered portion of the bone. The bone is secured by a plate and screws.

5 Claims, 10 Drawing Sheets

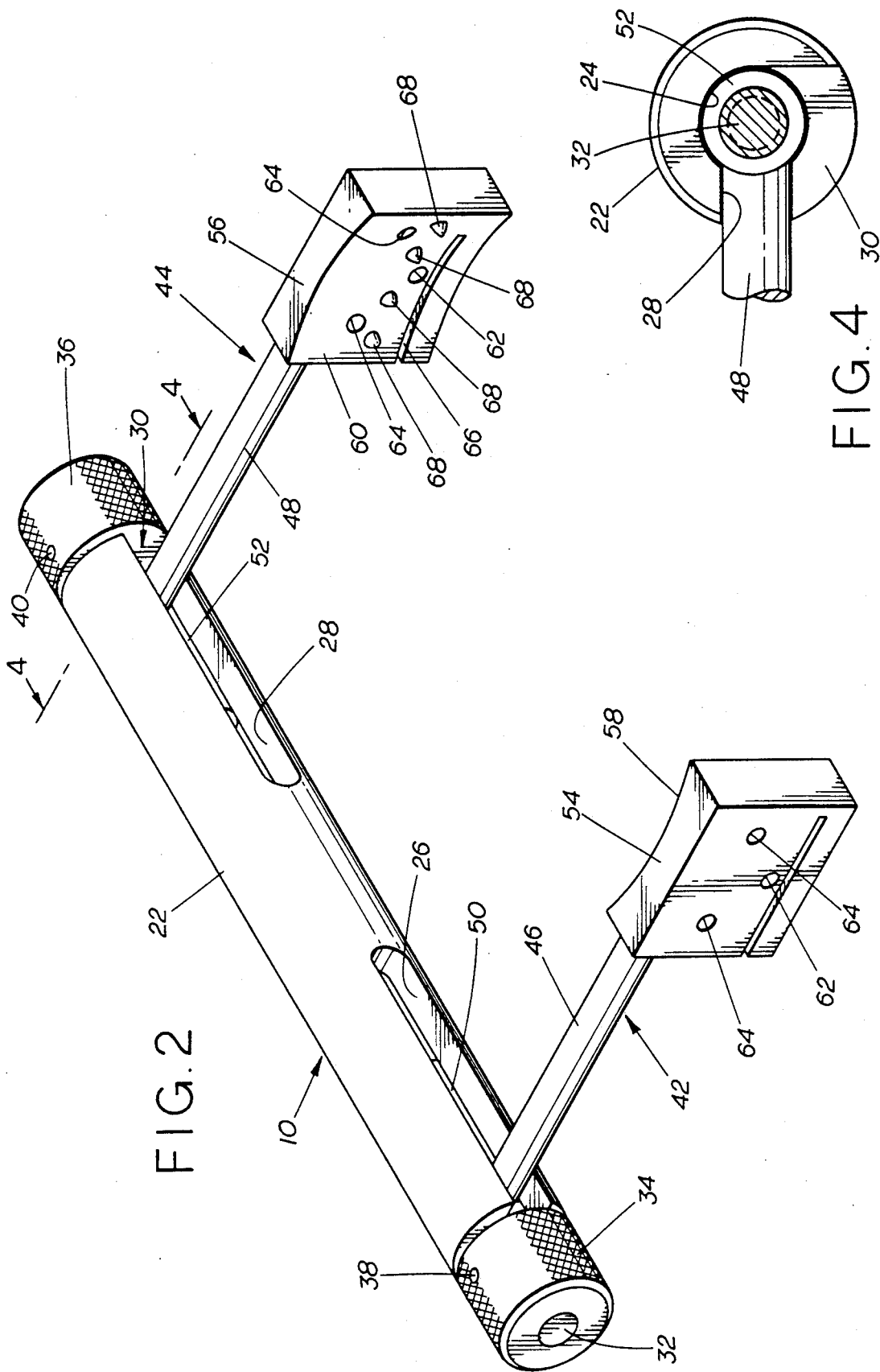

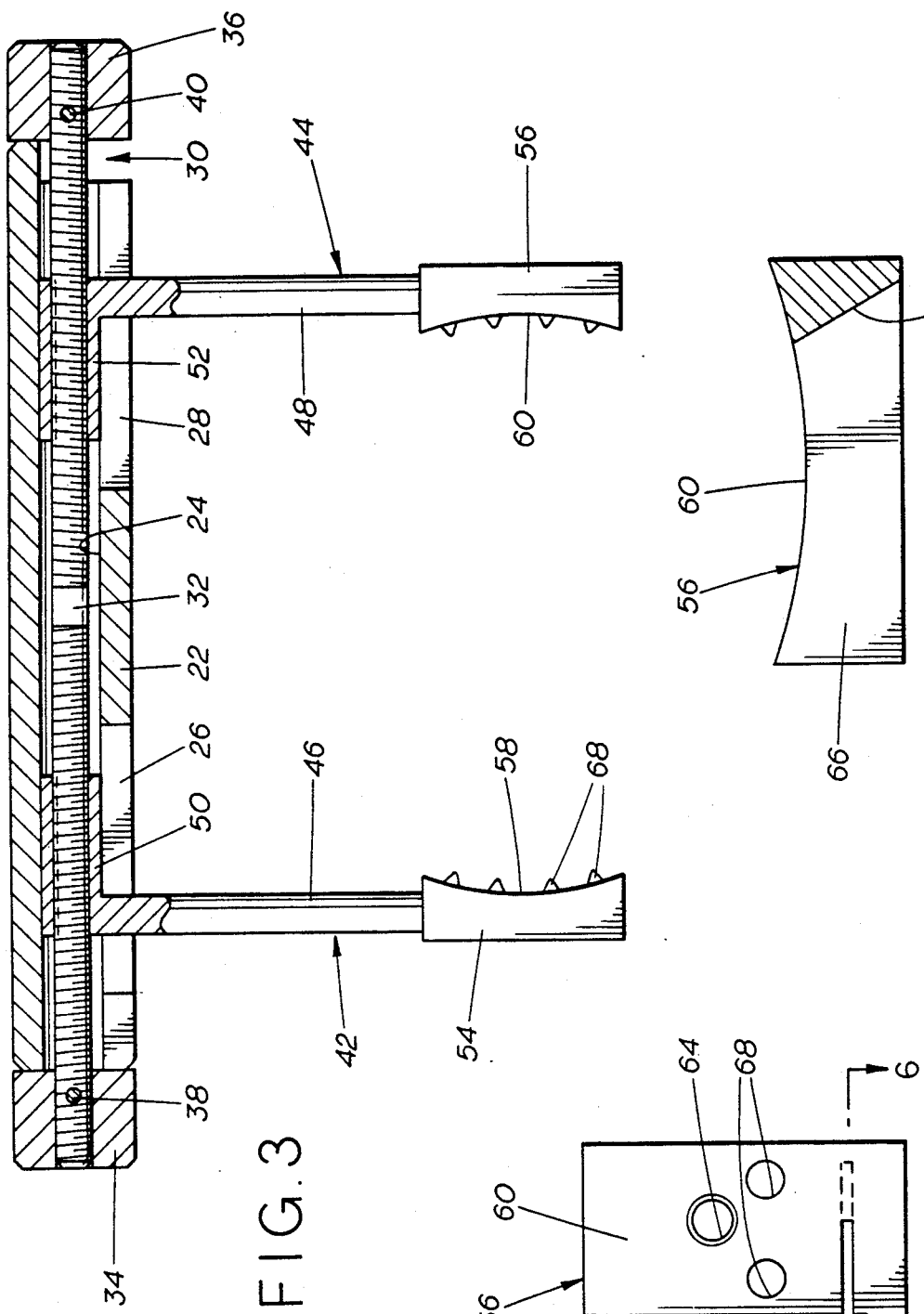
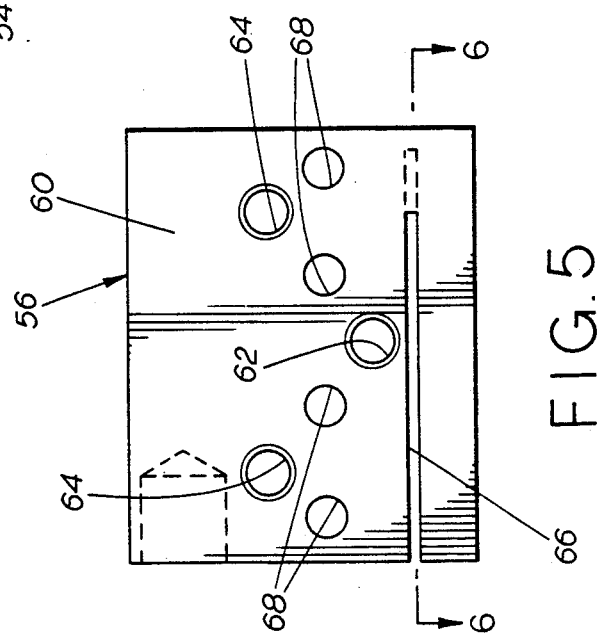

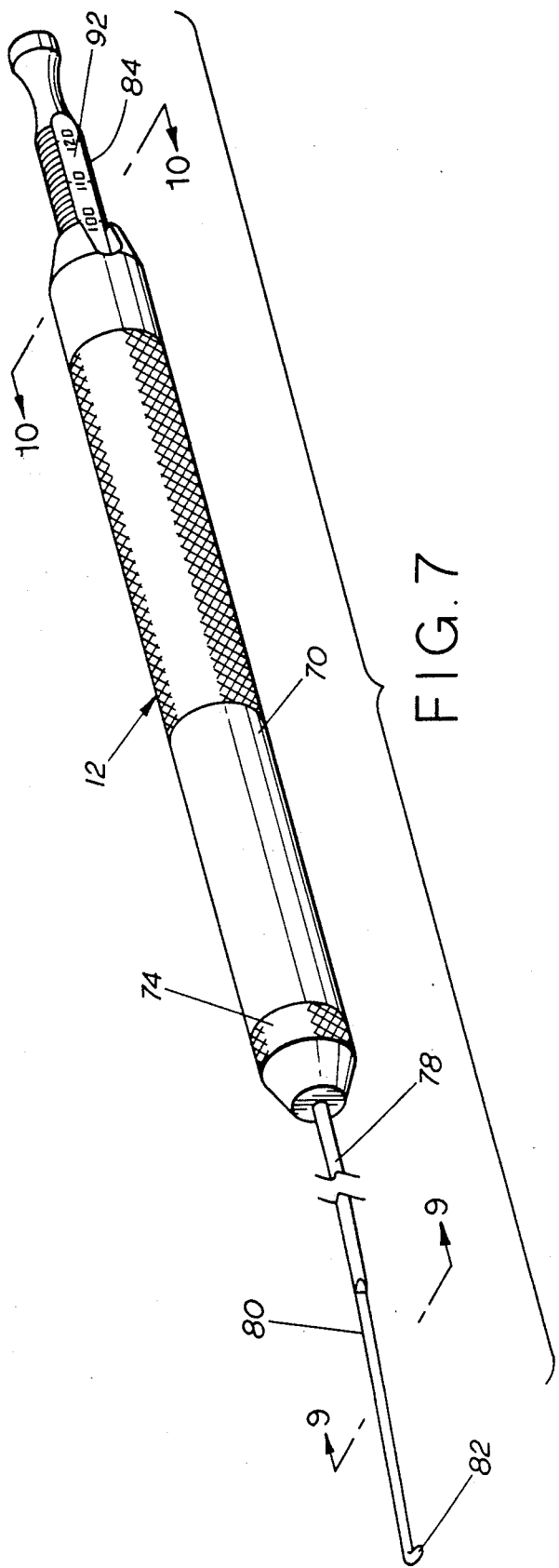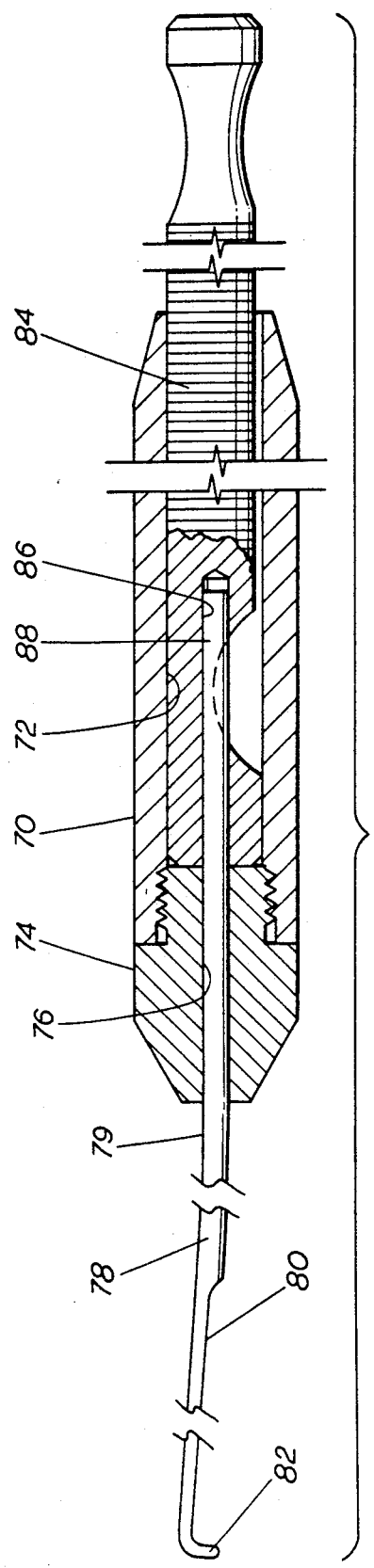

UPPER TIBIAL OSTEOTOMY SYSTEM

BACKGROUND OF THE INVENTION

The present invention pertains to both the method of performing an osteotomy as well as the apparatus for performing this operation with a high degree of accuracy.

PRIOR ART

It has been known that it is possible to correct certain bone-related problems by removal of a wedge of the bone so as to realign the remaining segments thereof. This osteotomy technique can serve to bring anatomic and mechanical axes together at the joint for relief of gonarthritis, for example. This operation is usually performed adjacent the end of a bone, such as in the head of the tibia, without removing the end surface or entire head, as would be the case for preparation of the bone for implantation of a total joint prosthesis, such as a total knee prothesis. It is important that the operation be performed with a high degree of accuracy so that the end surface of the bone is not damaged and is subsequently correctly realigned to the desired orientation with respect to the alignment of the anatomic and mechanical axes of the bone. In many ways this type of operation is much more difficult to perform than preparation for a total prosthetic implant, since engaging surfaces of the bone are to be left in place in an undamaged but realigned position. This reorientation is best accomplished by cutting a wedge from the bone so as to leave intact a segment joining both portions of the bone. The bone portions are then drawn together to close the wedge shaped gap so that the sides thereof engage. The bone is secured and allowed to heal in this new configuration. Clearly such an enterprise requires a great degree of accuracy in controlling both the depth of the first cut, to avoid completely severing the end of the bone, and in making the second cut to remove a precise wedge of bone necessary to achieve the desired angular reorientation of the end surface thereof.

SUMMARY OF THE INVENTION

The present invention includes both the method and apparatus for performing osteotomy, such as on an upper portion of a tibia, in order to reorient an end surface portion of a bone to properly align the anatomic and mechanical axes of abutting bones. The subject method begins with identifying the joint line and mounting a first guide assembly on the bone properly oriented with respect to the joint line. The first guide assembly is stabilized by drills placed into the bone. A bore is drilled through the bone, the bore orientation being controlled by the first guide. A depth gauge is then passed through the bore to accurately measure the transverse width of the bone. A cutting blade is introduced through a slot in the first guide to make a first cut into the bone. The first cut is preferably substantially parallel to the end surface of the bone and less than its transverse width. The first guide assembly is removed and a blade portion of a second guide assembly inserted into the first cut. The cutting blade is introduced into an appropriate slot of the second guide assembly and a second cut is made. The second cut will intersect the first cut to define a wedge shaped bone segment. The second guide assembly and bone segment are then removed. An "L" shaped buttress plate is applied to the bone with screws entering the stabilizing screw holes. An external compressor device is engaged with the plate and bone and used to draw the osteotomy closed by plastic deformation of the unsevered portion of the bone. The bone is then secured with more screws passing through the buttress plate.

The first guide assembly has a body member with an axial bore. A single threaded member extends through the bore and a pair of guide arm members are mounted thereon. As the screw is rotated, the guide arms are moved along the body, either relatively spreading or contracting in accordance with the direction of rotation of the screw. Both arm members have bone engaging plates, each with at least one bore for passage of stabilizing drills into the bone and a cutting blade guide slot. One arm member can also be arranged for limited rotation about the body to facilitate placement of the first guide assembly on a bone.

The second guide assembly has a flat blade extending fixedly from a body portion. The body portion defines a plurality of slots, each of which are parallel to the blade along their transverse axes but which are angled along their longitudinal axes so that a cutting blade introduced through any of the slots will intersect the flat blade at approximately the same location thereby defining wedges of like radius but different angles.

The depth gauge has a generally cylindrical body with an axial through bore. A plunger member is mounted in the bore with a measuring rod extending from one end and a scale from the other end. The extension of the measuring rod from the body is reflected on the scale.

The buttress plate is a generally L-shaped member profiled three dimensionally to lie against a bone head. The plate has a plurality of holes therein to receive screws to fix the plate to a bone.

The external compressor assembly is a pliers-like device formed by two arms pivotally attached together intermediate their ends. Like first ends of the arms are provided with engagement means to grip the buttress plate and bone. The opposite like second ends have, mounted therebetween, spring means and locking means, the former tensioning the arms and the latter adjustably securing the arm in relative fixed positions.

BRIEF DESCRIPTION OF THE DRAWINGS

The present invention will now be described by way of example with reference to the drawings in which:

FIG. 2 is a perspective view of the first guide assembly for transverse alignment;

FIG. 3 is a plan view, partially in section, of the first guide assembly;

FIG. 4 is an end view, partially in section, taken along line 4—4 of FIG. 2;

FIG. 5 is a side elevation of the inner face of a clampplate of the first guide assembly;

FIG. 6 is a section taken along line 6—6 of FIG. 5;

FIG. 7 is a perspective view of the depth gauge slide assembly of the present invention;

FIG. 8 is a foreshortened side elevation, partly in section, of the depth gauge slide assembly of the FIG. 7;

DETAILED DESCRIPTION OF THE PRESENT INVENTION

In the figures, like numbers refer to like parts throughout.

Figure 1:
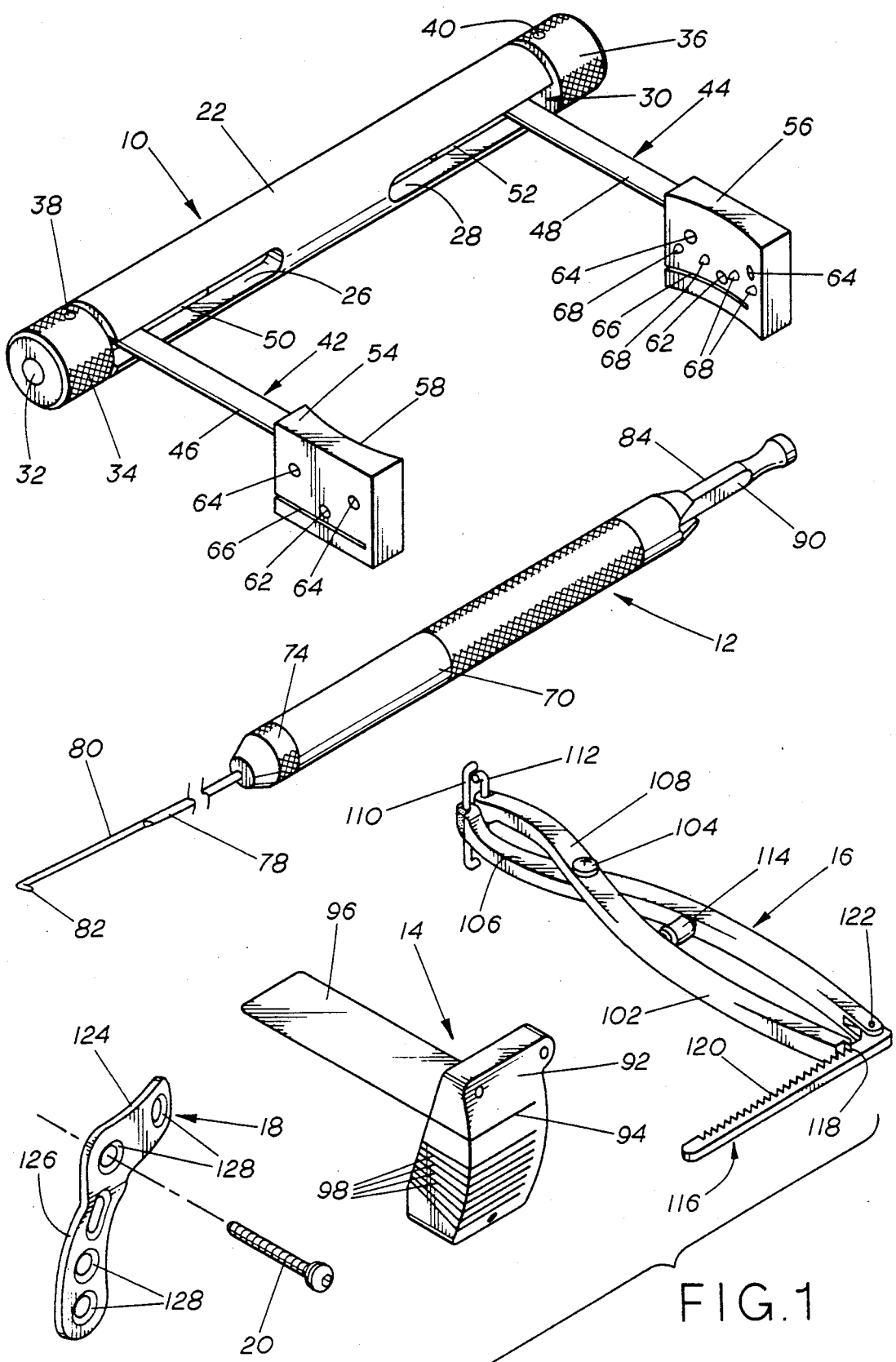
FIG. 1 is a perspective view of the components of the present invention.
Figure 9:
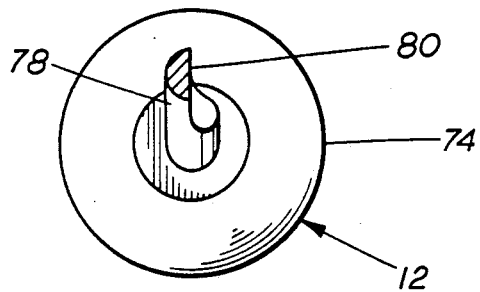
FIG. 9 is a section taken along line 9—9 of FIG. 7.
Figure 10:
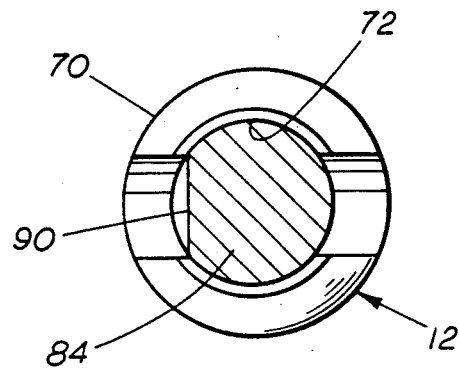
FIG. 10 is a section taken along line 10—10 of FIG. 7.
Figure 11:
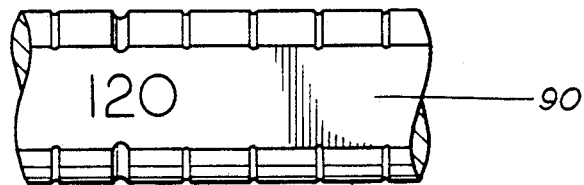
FIG. 11 is a detail of the scale face of the depth gauge slide assembly of FIG. 7.

The components of the present invention are shown in FIG. 1 and comprise a transverse alignment or first guide assembly 10, a depth gauge slide assembly 12, and an osteotomy second guide assembly 14, a compressor assembly 16, a buttress plate 18 and one or more bone screws such as bone screw 20. The detailed structure of each of these components will be discussed first and then their use in performing an upper tibial osteotomy will be described with reference to FIGS. 24 to 31.

Referring first to FIGS. 2 to 6, the transverse alignment or first guide assembly 10 has an elongated cylindrical body member 22 having an axial bore 24 extending completely therethrough. The bore is intersected at each end by longitudinal slots 26, 28 with the slot 28 having a radial extension 30 (see FIG. 4) extending approximately a quarter of the way around the circumference of the body 22. A threaded shaft 32 is mounted to extend through the bore 24 with knurled knobs 34, 36 held on opposite ends thereof by pins 38, 40, respectively. A pair of mirror image clamp arm assemblies 42, 44 are formed by arms 46, 48 having integrally fixed on one end thereof internally threaded cylinders 50, 52 extending normal to the axis of the arms and receiving the threaded shaft 32 therein. The outer dimensions of the cylinders 50, 52 are such as to allow free sliding movement in the bore 24. A clamp plate 54, 56 is fixed on the free end of the respective arms 46, 48, with each plate having an inwardly directed, slightly profiled, clamp face 58, 60. Each clamp plate is provided with a guide bore 62, a plurality of bores 64, and a guide slot 66, which are parallel to the axis of the cylindrical body member 22 and normal to the axis of the respective arm 46, 48 and displaced therefrom. Preferably the guide bores 62 and guide slots 66 are also axially aligned between the guide plates 54, 56. A plurality of gripping protuberances 68 extend from the guide face 58, 60. As seen in the sectional view of FIG. 6, the guide slot 66 has an oblique end wall 67 which is provided to minimize contact between the end wall 67 and a saw blade, the use of which is explained hereafter.

The depth gauge slide assembly 12 is shown in FIGS. 7 through 11. This assembly is formed by a generally cylindrical body 70 having a through-bore 72 with a cap 74 threaded on one end thereof. The cap 74 has a axial bore 76 through which an elongated measuring arm 78 extends. The the arm 78 is profiled at 80 to include a transversely extending lip 82 on the free end thereof. A scale arm 84 extends from the opposite end of the bore 72 and has an axial bore 86 which receives therein the opposite end 88 of the measuring arm 78. The scale arm 84 has a flattened surface 90 on which is inscribed a measuring scale (see FIG. 11). The measuring arm 78 has a slight bend 79 in it forcing the scale against the side of the cylinder body (as shown in FIG. 8). This creates a friction fit so that the arm and scale cannot move at random.

The osteotomy guide assembly is shown in FIGS. 12 to 15 and includes a body member 92 having a first slot 94 therein. A flat blade 96 is fixed in the first slot extending therefrom. A plurality of guide slots 98 are formed in the body 92 each slot 98 having parallel transverse axes and being offset from the first slot 94 by an angular displacement so that a cutting blade member passing through any of the slots 98 will intersect the flat blade 96 at approximately the same location 97 spaced from body 92 thereby defining wedge shapes of different angular dimensions. As seen in the sectional view in FIG. 15 and in phantom outline in FIG. !4, the slots 98 have an oblique end wall 99 which is provided to minimize contact between the end wall 99 and the saw blade.

Figure 16:
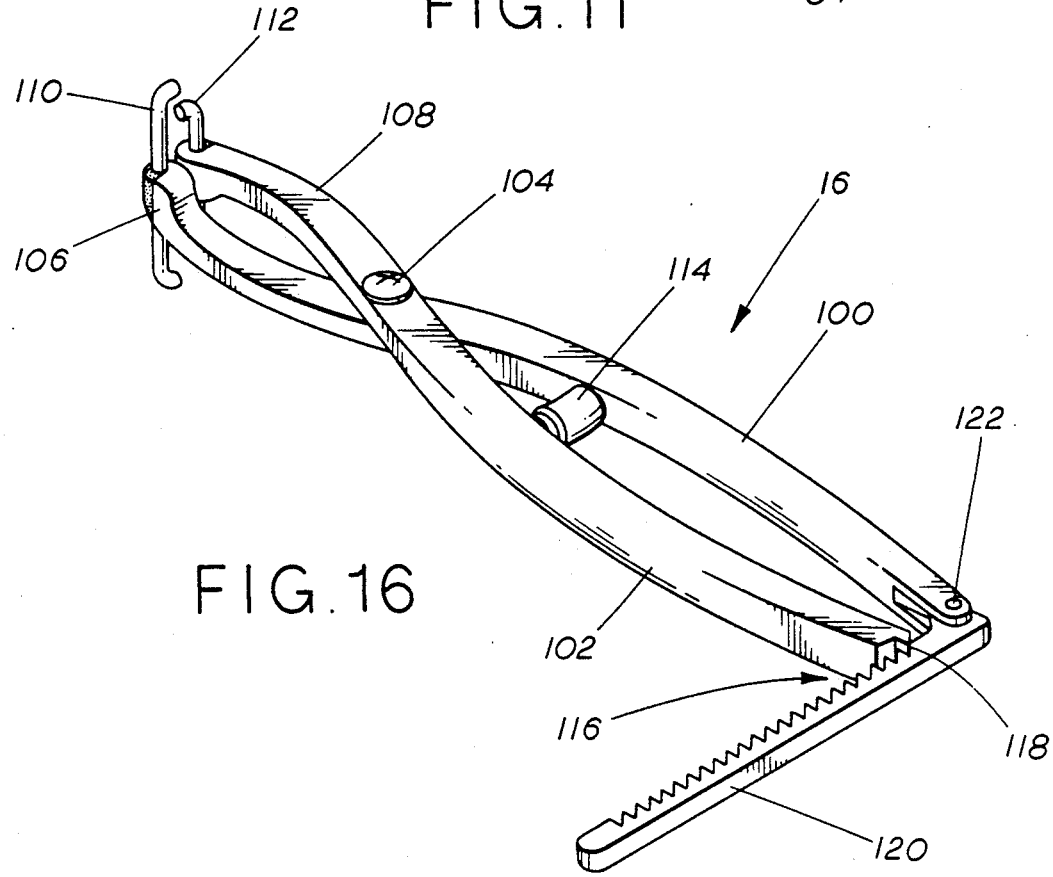
FIG. 16 is a perspective view of the external compressor assembly.
Figure 12:
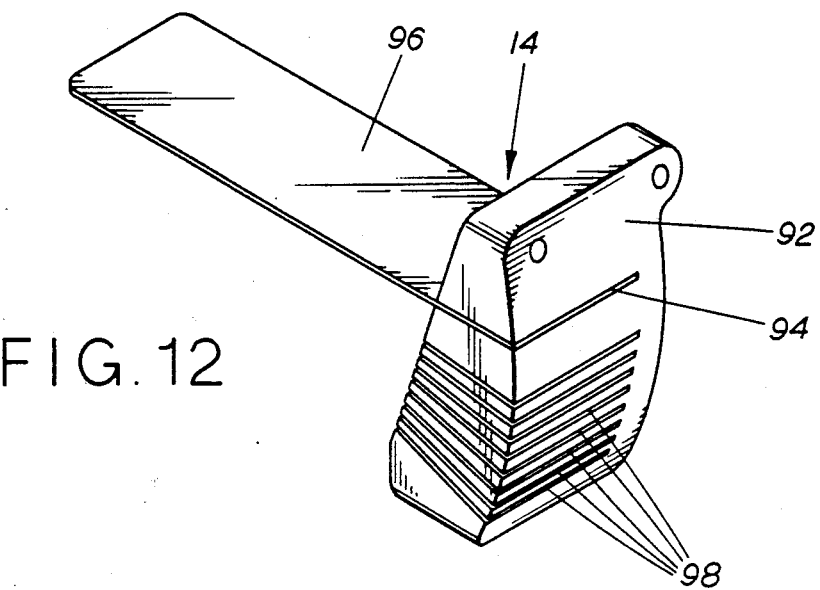
FIG. 12 is a perspective view of the osteotomy second guide assembly.
Figure 13:
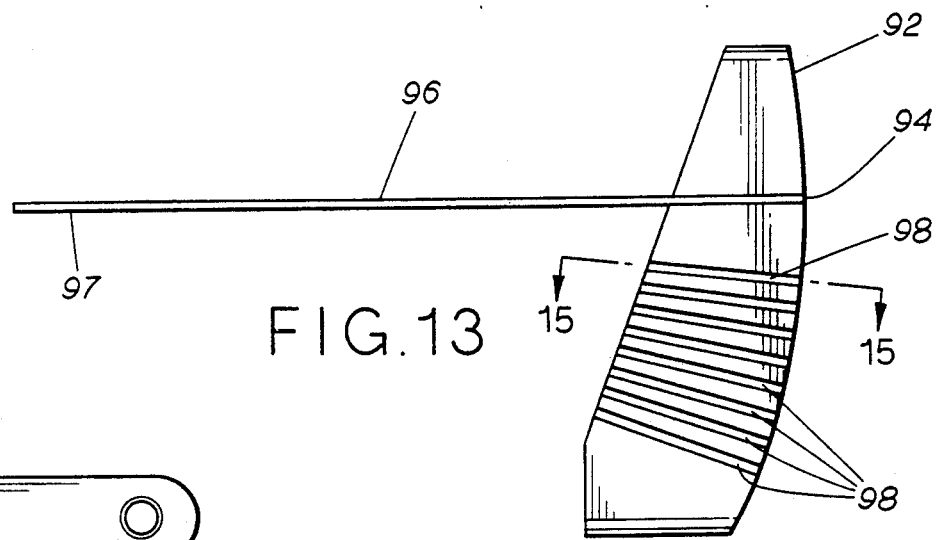
FIG. 13 is a side elevation of the osteotomy second guide assembly.
Figure 14:
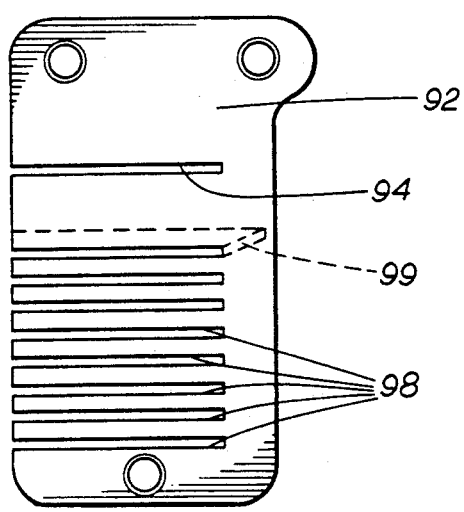
FIG. 14 is a end elevation of the guide body member of the second guide assembly.
Figure 15:
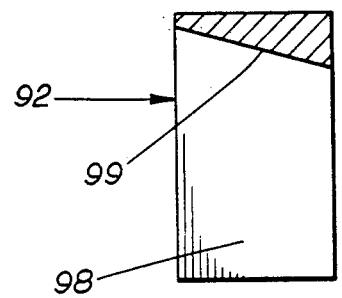
FIG. 15 is a section taken along line 15—15 of FIG. 13.
Figure 18:
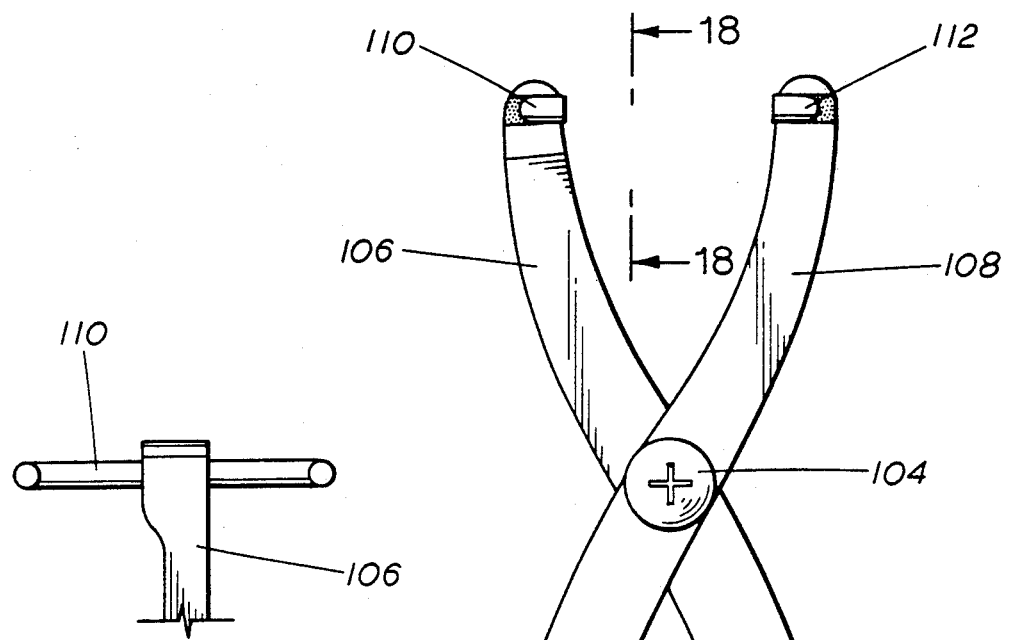
FIG. 18 is a detail of the compressor assembly.
Figure 17:
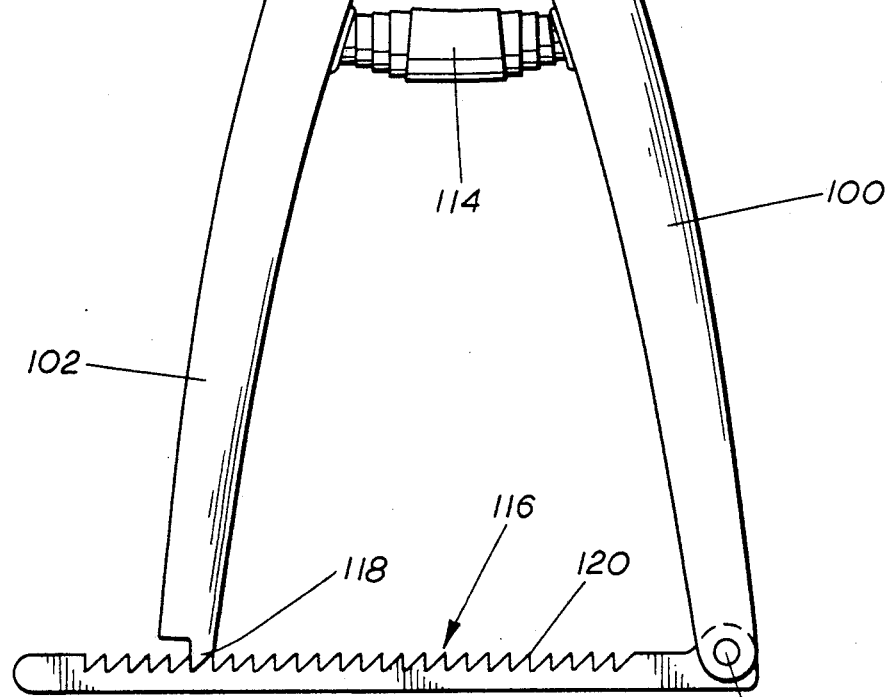
FIG. 17 is a plan view of the compressor assembly of FIG. 16.

The compressor assembly 16 is shown in FIGS. 16 to 18 and includes arms 100, 102 pivotally attached intermediate their ends by pivot pin 104. First like ends 106, 108 of the arms 100, 102 are provided with profiled bars 110, 112, respectively. These bars are shown generally as rods with slightly curved end portions for grippingly engaging the bone surface and holes in the buttress plate 18. The bone engaging arm 110 is preferably slightly longer than the plate engaging arm 112. Spring 114 is mounted between arms 100, 102 towards their second ends which are provided with a ratchet assembly 116 including fixed powl 118 on arm 102 and rack 120 pivotally attached to arm 100 by pin 122.

Figure 19:
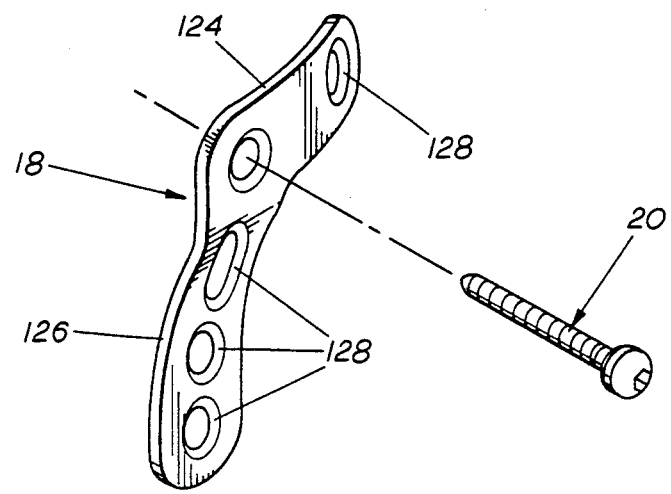
FIG 19 is a perspective view of the buttress plate with a fixation screw exploded therefrom.
Figure 21:
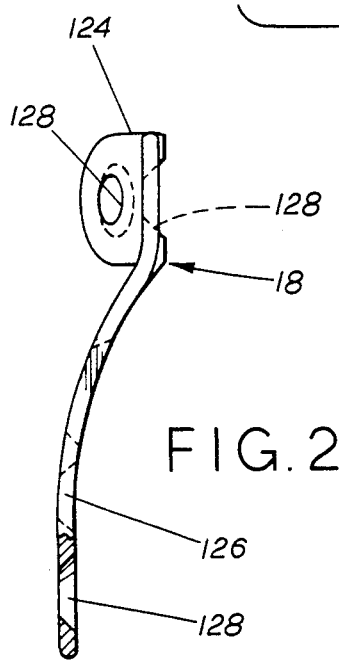
FIG. 21 is an end elevation of the buttress plate.
Figure 20:
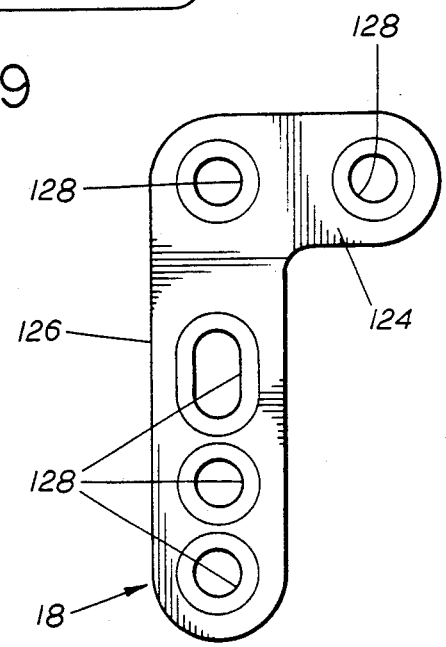
FIG. 20 is a side elevation of the buttress plate.

The buttress plate 18 is shown in FIGS. 19 to 21 and is generally an L-shaped member having a first arm 124, a second arm 126, and a plurality of through-bores 128. It will be appreciated from the perspective view in FIG. 19 and the end elevation in FIG. 20 that the buttress plate is not planar but is profiled to conform to the upper portion of a tibia. The plate is made of any of the known biocompatible metals.

Figure 22:
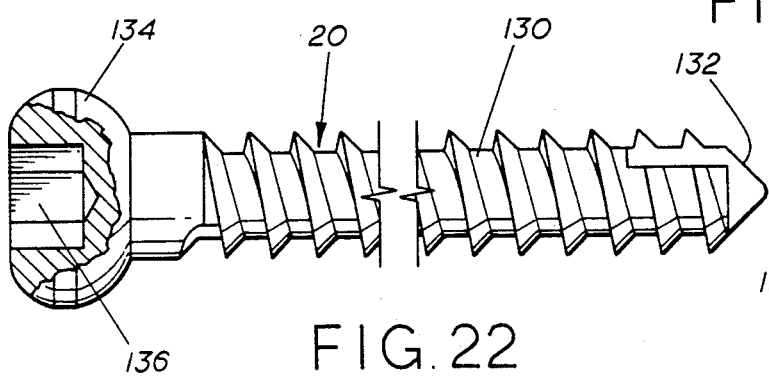
FIG. 22 is a side elevation, partly in section, of a bone screw used with the present invention.
Figure 23:
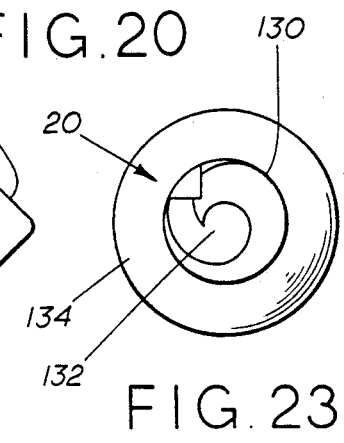
FIG. 23 is an end view of the bone screw of FIG. 22.

FIGS. 22 and 23 show a bone screw 20 of the type used with the present invention. Each screw 20 is formed from a biocompatible metal and has a threaded shank 130 with a self-tapping end 132 and a head 134 with a drive recess 136, in this case a hexagonal recess.

The operation of the present invention will now be described by way of example with reference to FIGS. 24 to 31.

Figures 24, 25:
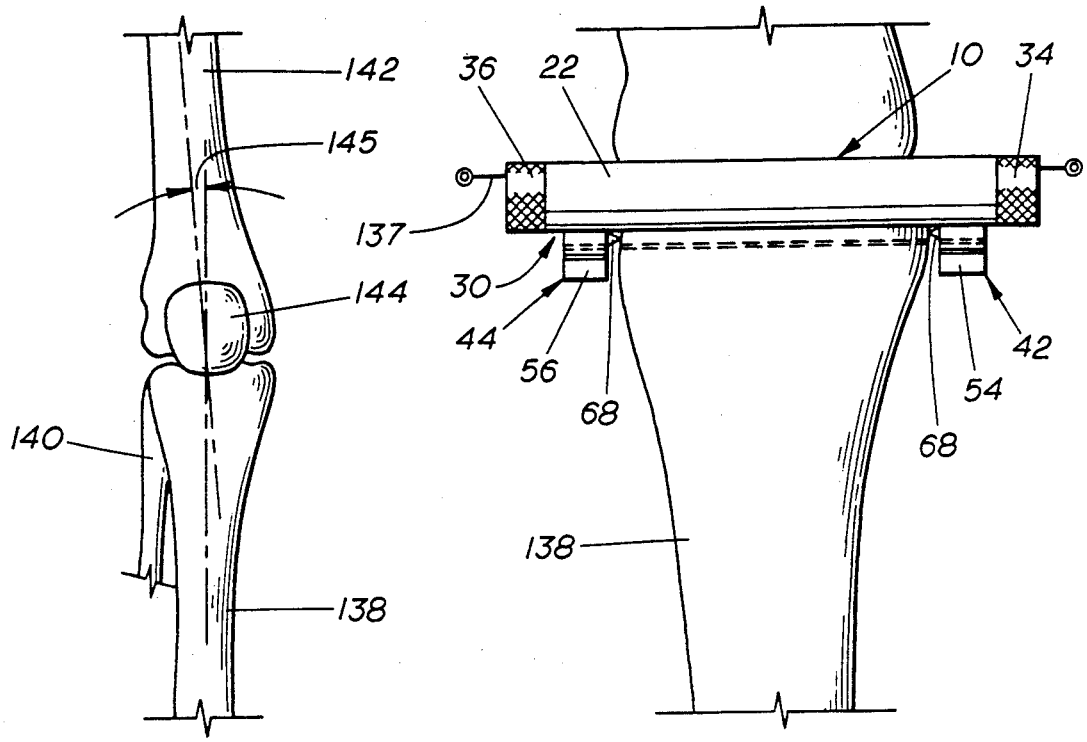
FIGS. 24–31 show the sequence of use of the components of the present invention as they would be utilized to perform an upper tibial osteotomy according to the subject method.

FIG. 24 shows a typical knee joint formed by a tibia 138, a fibula 140, a femur 142, and a patella 144. Under the normal conditions, there is an angular offset 145 between the anatomic axes of the tibia and the femur. In the instance shown, which is a right leg, this angle is not of sufficient magnitude, for any one of a number of reasons, so that the mechanical axis does not pass substantially through the intersection of the anatomic axes at the joint.

Figure 26:
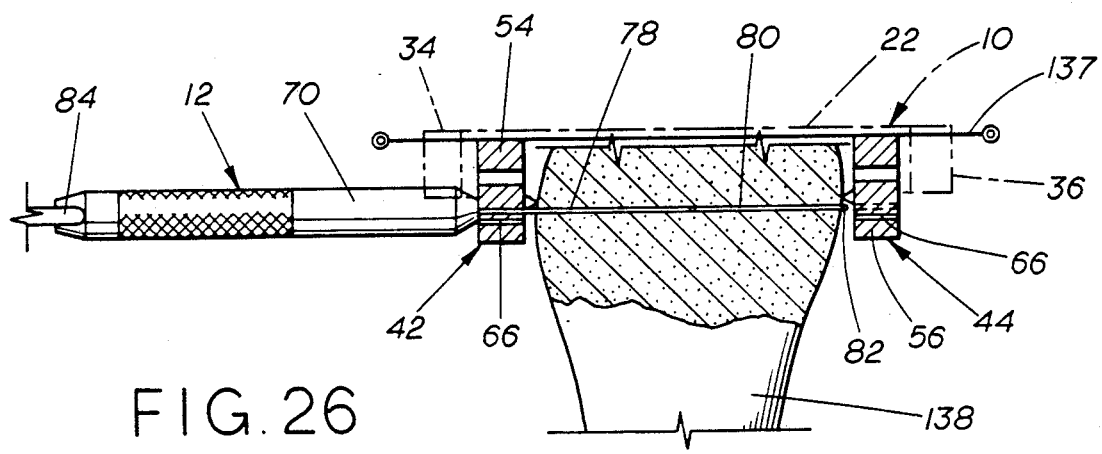
Figure 27:
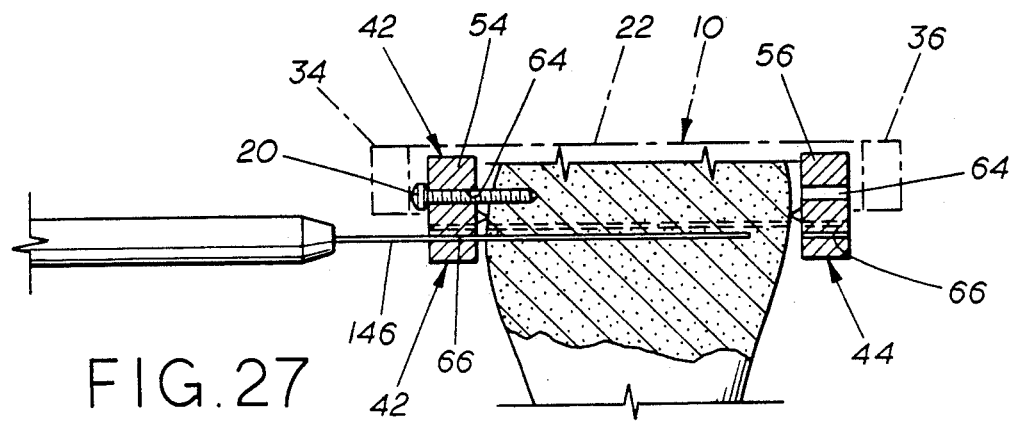

The joint is surgically exposed and the joint line indentified using tibial locating needles 137. The transverse alignment or first guide assembly 10 is positioned mediolaterally on the upper tibia 138, as shown in FIG. 25, with the upper end of the assembly touching the tibial locating needles. The clamp arm 44 can be swung to a position almost normal to the clamp arm 42, by virtue of the slot 30 in order to facilitate this mounting of the assembly on the tibia. The two clamp plates 54, 56 are brought into engagement with opposite sides of the tibia by rotation of the knobs 34, 36 driving cylinders 50, 52 along the threaded shaft 32. They are tightened until the assembly is firmly positioned on the tibia with the protrusions 68 providing a biting grip. The assembly is stabilized by drills 19 inserted into the bone through holes 64. Next a transverse bore is drilled completely through the tibia using one of the guide holes 62. The depth gauge slide assembly 12 is used, as shown in FIG. 26, to measure the width of the bone. With the body 70 pressed against the near side of the guide plate 54, the measuring arm 78 is passed completely through the tibia and hooked on the far side to obtain an accurate measurement as to the bone width by reading the scale 90. This is an important measurement since it is the desire not to completely sever the top of the tibia, as would be the case in preparation for a total knee replacement prosthesis. A cutting blade 146 is then inserted through guide slot 66 to make a cut in the tibia to the depth chosen, which depth is less than that measured by the depth gauge slide assembly, see FIG. 27. It will be seen from FIG. 27 that the top of the tibia is not completely severed. The cutting blade 146 is removed and the first guide assembly 10 is also removed.

Figure 28:
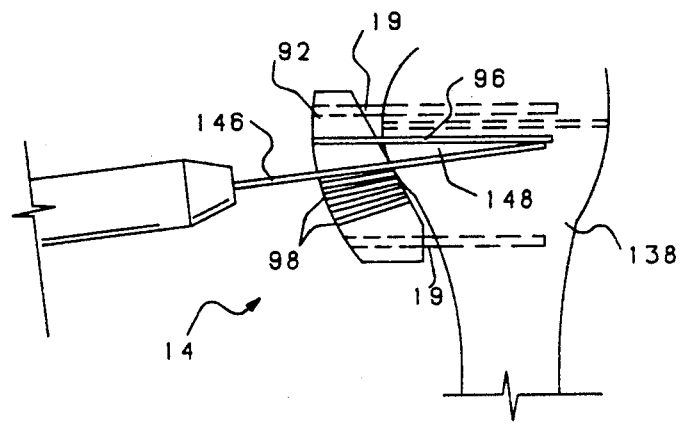
Figure 29:
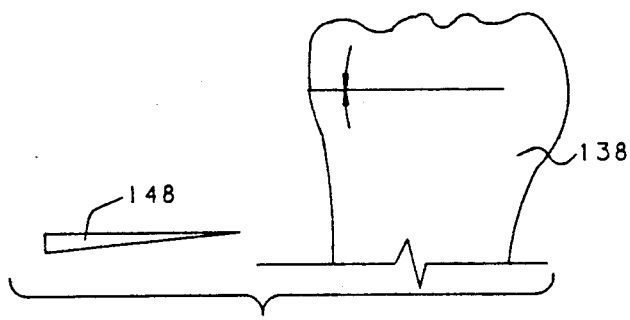
Figure 30:
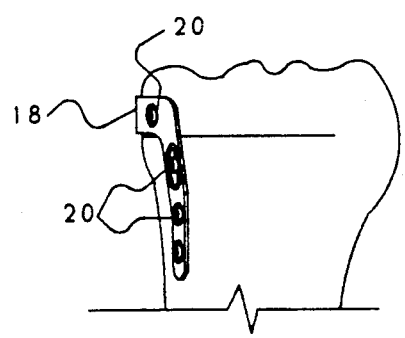
Figure 31:
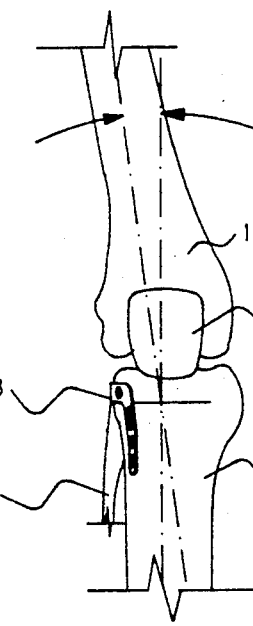

The blade 96 of the osteotomy or second guide assembly 14 is inserted into this first cut. This guide assembly 14 is stabilized by placing it on the same drills as were used for the first guide with the blade fitting in the slot cut by the first guide as shown in FIG. 28. The cutting blade 146 is then introduced through one of the slots 98 to cut a wedge-shaped section 148 from the tibia 138. The wedge-shaped section 148 is removed, along with the osteotomy guide assembly 14. A buttress plate 18 is fixed to the tibia with screws 20 entering the same holes used to stabilize the first guide assembly. The compressor assembly 16 is then clamped against the bone and the buttress plate to apply pressure to close the osteotomy. To use the compressor assembly, a hole can be made in the tibia below the wedge-shaped section. One end of the bone engaging bar 110 is inserted in the hole, in the bone and a corresponding end of the plate engaging bar 112 is placed in a hole in the buttress plate 18. Closing the osteotomy usually takes several minutes, and repeated tightening of the compressor assembly, as it is the object to plastically deform the bone rather than fracture the unsevered segment. When the tibia has reached the condition shown in FIGS. 29 and 30 a screw is placed to hold the plate 18 in place. Then the compressor assembly 16 is removed and the buttress plate 18 is secured with additional screws to assure that the tibia will be held in proper alignment while new bone growth forms. It will be appreciated, from a comparison of FIGS. 24 and 31, that the present invention has accomplished the desired reestablishment of the proper angular relationship between the femur and the tibia.

The present invention may be subject to many modifications and changes without departing from the spirit or essential characteristics thereof. The present invention is therefore to be deemed in all respects as illustrative and not restrictive of the scope of the invention.

What is claimed is:

1. A surgical kit for performing an upper tibia osteotomy, said kit comprising:

a transverse alignment guide assembly having at least one cutting blade alignment slot for guiding a cutting blade to cut a first slot in a tibia;

an osteotomy guide comprising mounting means for attaching the guide in a predetermined relation to the first cut, said osteotomy guide having a plurality of aligned parallel cutting blade slots formed therein, said slots being angularly offset from the first slot so that a cutting blade passing through any one of the cutting blade slots will intersect the first slot thereby defining wedge shaped bones of different angular dimensions; and a fixation plate adapted to be secured to the tibia and to hold surfaces of the tibia created by the first and second cuts in proper relationship to each other during the healing of the tibia by new bone growth.

2. A surgical kit according to claim 1 wherein the mounting means further comprises an elongated blade member sized to be mounted in the first cut.

3. A surgical kit according to claim 2 wherein the transfer alignment guide assembly further comprises an elongated body member and two clamping arms adjustably mounted at opposite ends of said body member, said clamping arms for engaging opposite sides of said tibia head in gripping relation.

4. A surgical kit according to claim 3 wherein the transverse alignment guide assembly further comprises at least one measurement bore hole, and wherein the surgical kit futher comprises a measurement assembly for measuring the depth of the tibia through the measurement bore hole.

5. A surgical kit according to claim 4 further comprising a clamp assembly adapted to apply compressive forces to a first portion of the tibia above the first cut and to a second portion of the tibia below the second cut to draw the surfaces of the tibia created by the first and second cuts together.

* * * * *